(12) United States Patent
Hobeika et al.

(10) Patent No.: US 11,523,849 B2
(45) Date of Patent: Dec. 13, 2022

(54) SURGERY CONTROL TOOL FOR SPINAL CORRECTION ROD

(71) Applicant: EOS IMAGING, Paris (FR)

(72) Inventors: Joe Hobeika, Paris (FR); David Invernizzi, Serre les Sapins (FR); Arnaud Grivet, Besancon (FR)

(73) Assignee: EOS IMAGING, Paris (FR)

( * ) Notice: Subject to any disclaimer, the term of this patent is extended or adjusted under 35 U.S.C. 154(b) by 455 days.

(21) Appl. No.: 16/609,762

(22) PCT Filed: May 3, 2017

(86) PCT No.: PCT/IB2017/000698
§ 371 (c)(1),
(2) Date: Oct. 31, 2019

(87) PCT Pub. No.: WO2018/203101
PCT Pub. Date: Nov. 8, 2018

(65) Prior Publication Data
US 2020/0060734 A1    Feb. 27, 2020

(51) Int. Cl.
*A61B 17/70* (2006.01)
*A61B 90/90* (2016.01)
*A61B 90/00* (2016.01)
*A61B 17/00* (2006.01)

(52) U.S. Cl.
CPC ........ *A61B 17/7079* (2013.01); *A61B 17/708* (2013.01); *A61B 90/90* (2016.02); *A61B 2017/0023* (2013.01); *A61B 2017/00526* (2013.01); *A61B 2090/0807* (2016.02)

(58) Field of Classification Search
CPC combination set(s) only.
See application file for complete search history.

(56) References Cited

U.S. PATENT DOCUMENTS

| 2007/0093846 A1* | 4/2007 | Frigg | A61B 17/025 606/90 |
|---|---|---|---|
| 2012/0059420 A1 | 3/2012 | Hansen | |
| 2014/0107659 A1 | 4/2014 | Walters et al. | |
| 2015/0066088 A1 | 3/2015 | Brinkman et al. | |

FOREIGN PATENT DOCUMENTS

| WO | 2006/125029 A2 | 11/2006 |
|---|---|---|
| WO | 2007/092876 A2 | 8/2007 |
| WO | 2012054737 A1 | 4/2012 |
| WO | 2017001851 A1 | 1/2017 |

OTHER PUBLICATIONS

International Search Report, dated Jan. 15, 2018, from corresponding PCT application No. PCT/IB2017/000698.

* cited by examiner

*Primary Examiner* — Sameh R Boles
(74) *Attorney, Agent, or Firm* — Nixon & Vanderhye

(57) ABSTRACT

Disclosed is a surgery control tool: being no patient implant, including: an elongated body having the shape and the size of a spinal correction rod, end contact parts being able to contact a patient implanted spinal correction rod implant, spacers extending from the elongated body towards the end contact parts.

23 Claims, 9 Drawing Sheets

3/4 rear side view

SURGERY CONTROL TOOL FOR SPINAL CORRECTION ROD

FIELD OF THE INVENTION

The invention relates to the field of spinal correction rod, preferably to correct patient scoliosis.

BACKGROUND OF THE INVENTION

In the specific case of spinal arthrodesis surgery applied to treat scoliosis or degenerative spine deformations most of the surgeons are used to cut and bend the rods directly during the surgery for long segment spinal fixations. Therefore, spinal correction rod implants are implanted or implemented in patient body, more precisely in the neighbourhood of patient spine, implanted or implemented being alternatively used with the same meaning in the following text.

The surgeons usually have to apply successive in situ corrections to the shape of the rods and to make some X-ray radiographic to check the spinal correction.

According to a prior art, in the field of spinal correction rod, it is known to plan, with planning software, the shape and the size of a spinal correction rod to be used as an implant within the body of a patient.

The shape and the size of this spinal correction rod implant is the output of the planning software. This output is under the form of a first predetermined and organized set of numerical values being representative of the shape and the size of this planned spinal correction rod implant before implementation and a second predetermined and organized set of numerical values being representative of the shape and the size of this planned spinal correction rod implant after implementation.

The surgeon receives both a long and straight metal rod and a first paper containing this first set of numerical values representative of the shape and the size of this planned spinal correction rod implant before implementation as well as a second paper containing this second set of numerical values representative of the shape and the size of this planned spinal correction rod implant after implementation. After reading this first set of numerical values representative of the shape and the size of this planned spinal correction rod implant, the surgeon has in mind the size and the shape of the desired spinal correction rod implant, and the surgeon cuts the received rod to make it have the right size, and then bends it to make it have the right shape, to get at the desired spinal correction rod implant having both the right size and the right shape. Similarly, after having implemented this spinal correction rod implant, previously correctly cut and bent according to the first set of numerical values, the surgeon reads the second set of numerical values representative of the shape and the size of this spinal correction rod implant as it should be when implemented in patient body, the surgeon has in mind the size and the shape of the desired spinal correction rod implant as implemented, and the surgeon checks whether the cut and bent rod implemented in patient body has the right shape and the right size. First set of values and second set of values will be similar and close to each other.

SUMMARY OF THE INVENTION

The object of the present invention is to alleviate at least partly the above mentioned drawbacks.

More particularly, the invention aims to provide a surgery control tool helping the surgeon to check the shape and size of the spinal correction rod implant once implemented in a patient body, such surgery control tool being simple and efficient to use for the surgeon, and presenting a better compromise between simplicity and efficiency than the old paper containing merely a set of numerical values representative of the spinal correction rod implant as implemented in patient body did. This surgery control tool will be a real tool helping directly the surgeon, and not only processing instructions to the surgeon helping him indirectly by telling him how he should proceed when checking the shape and the size of the spinal correction rod implant implemented in patient body.

More particularly, the invention aims to provide a surgery control tool helping the surgeon to better visualize the differences between on the one side the spinal correction rod implant as implemented in patient body and on the other side the surgery control tool corresponding to the spinal correction rod implant as it should have been implemented in patient body, and thereafter to reduce as much as possible such differences by bending again one or both of spinal correction rod implants as implemented while keeping them in place as implemented or by taking them out (then cutting again is also possible), bending them again and replacing them for further control by the surgery control tool according to the invention.

More particularly, the invention aims to provide a surgery control tool helping the surgeon to better visualize the differences between on the one side the spinal correction rod implant as implemented in patient body and on the other side the surgery control tool corresponding to the spinal correction rod implant as it should have been implemented in patient body, by providing for a surgery control tool outside patient body which has similar shape and size as the spinal correction rod implant implemented in patient body which is at least less visible or even has become (at least partly) hardly visible for the surgeon.

This object is achieved with a surgery control tool, being no patient implant, comprising: an elongated body having the shape and the size of a spinal correction rod, end contact parts being able to contact a patient implanted spinal correction rod implant, spacers extending from said elongated body towards said end contact parts.

The elongated body has the shape and the size of a spinal correction rod. Depending on the disposition of the spacers, either the elongated body has the shape and the size of the spinal correction rod it is supposed to control, or the elongated body has the shape and the size of a spinal correction rod which is slightly different from the spinal correction rod it is supposed to control. Then, the spinal correction rod the elongated body has the shape and size of, is the same way also slightly different from the patient implanted spinal correction rod implant.

In the case where the elongated body has the shape and the size of a spinal correction rod which is slightly different from the spinal correction it is supposed to control, the control operation can still be very precise, because first the slight difference of shape and/or size between the surgery control tool and the spinal correction rod to be controlled is very small, because of relatively large radii of curvature along said spinal correction rod to be controlled, and second it is anyway compensated for by the disposition of the spacers.

Preferably, either the surgery control tool has the size and the shape of a patient specific spinal correction rod or the surgery control tool has the size and the shape of an orthogonal shift of this patient specific spinal correction rod.

Preferably, either the surgery control tool has the length and the curvature of a patient specific spinal correction rod or the surgery control tool has the length and the curvature of an orthogonal shift of this patient specific spinal correction rod.

For example, spacers being both orthogonal to elongated body and to spinal correction rod, will lead to a slight difference of shape and/or size between said elongated body and said spinal correction rod to be controlled, thanks to this specific disposition of the spacers, when the spinal correction rod will be exactly shaped and sized as expected, then the slightly differently shaped and/or sized elongated body of surgery control tool will rest exactly on said spinal correction rod to be controlled, via the spacers, each of its end contact parts touching said spinal correction rod to be controlled.

This object is also achieved with a pair of surgery control tools according to the invention, wherein one of said surgery control tools has the shape and the size of a spinal correction rod adapted to be implemented on one side of patient spine whereas the other of said surgery control tools has the shape and the size of a spinal correction rod adapted to be implemented on the other side of patient spine. This way, both spinal correction rods, both implants may be checked by the surgeon when having been implemented in patient body by the surgeon too, using a pair of similar surgery control tools, one per spinal correction rod implant, thereby doubling the global gain in simplicity and efficiency that is gained with using only a single tool for only one of the spinal correction rod implants.

This object is again achieved with a kit comprising: a surgery control tool or a pair of surgery control tools according to the invention, a printed document or an electronic document including patient specific spinal correction information corresponding to said surgery control tool or to said pair of surgery control tools. This way, the surgeon has at her or his disposal, both the helping surgery control tool making surgery checking simpler and more efficient for her or him, and also all or part of the set of numerical values representative of the spinal correction rod implant as in the prior art. This is more secure, since it allows the surgeon to crosscheck both pieces of information in order to more easily detect any possible mistake when checking implementation of spinal correction rod implants.

This object is still achieved with a manufacturing method of a surgery control tool having the shape and the size of a spinal correction rod but being no patient implant, comprising: a first step of making two 2D X-ray patient images, a second step of making a patient specific 3D spinal reconstruction from said two 2D X-ray patient images, a third step of determining a patient specific spinal correction, a fourth step of making a surgery control tool or a pair of surgery control tools, according to the invention, having the shape and the size of a patient specific spinal correction rod implant but being no patient implant.

According to the invention, the proposed surgery control tool aims at proposing a 3D template set to help the surgeons to apply a surgery checking correction in-situ.

According to embodiments of the invention, no investment is needed in a navigation system, what reduces costs, simplifies the surgery and optimizes surgery time.

According to embodiments of the invention, numerous radiographic X-ray images for intra-operative curvature measurements are saved, thereby also saving radiation dose for the patient and reducing intra-operative imaging costs.

Preferred embodiments comprise one or more of the following features, which can be taken separately or together, either in partial combination or in full combination, with one or more of preceding objects of the invention.

Preferably, most of, preferably all of, said spacers extending from said elongated body, extend parallel to one another. This way, the surgery control tool with parallel spacers is easier and cheaper to manufacture.

Preferably, most of, preferably all of, said spacers extending from said elongated body, extend vertically when said surgery control tool end contact parts contact said patient implanted spinal correction rod implant. This way, the surgery control tool with vertical spacers is easier and cheaper to manufacture.

Preferably, most of, preferably all of, said spacers extending from said elongated body, have the same length. This way, the surgery control tool with vertical spacers is easier and cheaper to manufacture.

Preferably, most of, preferably all of, said spacers disposed along said elongated body, are longitudinally immobile relative to said elongated body. This way, the surgery control tool with vertical spacers is easier and cheaper to manufacture.

Preferably, most of, preferably all of, said spacers extending from said elongated body, extend orthogonally from said elongated body. This way, the surgery control tool with orthogonal spacers allows for the surgeon to more precisely check the correctness of the curvature of the patient implanted spinal correction rod implant.

Preferably, most of, preferably all of, said spacers extending from said elongated body, have different lengths depending on the curvature radius respectively at their junction points with said elongated body. This way, the surgery control tool with orthogonal spacers and different lengths allows for the surgeon to more precisely check the correctness of the curvature of the patient implanted spinal correction rod implant.

Preferably, most of, preferably all of, said spacers extending from said elongated body, extend both orthogonally from said elongated body and orthogonally from said patient implanted spinal correction rod implant. This way, the surgery control tool with orthogonal spacers allows for the surgeon to much more precisely check the correctness of the curvature of the patient implanted spinal correction rod implant. This is the most preferred embodiment of the invention.

Preferably, most of, preferably all of, said spacers extending orthogonally from said elongated body and orthogonally from said patient implanted spinal correction rod implant, have the same length. This way, the surgery control tool with orthogonal spacers allows for the surgeon to much more precisely check the correctness of the curvature of the patient implanted spinal correction rod implant. This is a most preferred realization of the most preferred embodiment of the invention.

Preferably, average length of said spacers ranges from 35 mm to 45 mm, preferably ranges from 38 mm to 42 mm. This way, the surgery control tool allows for the surgeon to simultaneously first keep the bulk of the surgery control tool to a reasonable extent making it easy to use and second improve the visibility of the elongated body of the surgery control tool making this elongated body clearly visible to the surgeon although the patient implanted spinal correction rod implant on which it rests is much less or even hardly visible to the surgeon. The usually required angular precision for surgeons being about plus or minus 3 degrees, this leads to a precision of about 1 mm for the central spacer length of the surgery control tool.

Preferably, most of, preferably all of, said spacers disposed along said elongated body, are longitudinally mobile relative to said elongated body. This way, spacers can better adapt to avoid bumping into screw heads being screwed in patient spine to guide and hold patient implanted spinal correction rod implant via a slit in each screw head. This longitudinal mobility range will be all the less detrimental to the global precision of the surgery control tool that the geometry of the spacers leads to an intrinsically more precise surgery control tool.

Preferably, said longitudinal mobility range is less than 8 mm, preferably less than 6 mm, and/or wherein said longitudinal mobility range is more than 2 mm. This way, most of required adjustments may be performed to the cost of a limited longitudinal mobility range, rather easy and cheap to implement in the surgery control tool.

Preferably, said longitudinal mobility range is less than 15 mm, preferably less than 10 mm, and/or wherein said longitudinal mobility range is more than 4 mm, preferably more than 7 mm. This way, all of required adjustments may be performed to the cost of a limited longitudinal mobility range, rather easy and cheap to implement in the surgery control tool. This longitudinal mobility range will be all the less detrimental to the global precision of the surgery control tool that the geometry of the spacers leads to an intrinsically more precise surgery control tool.

Preferably, said elongated body is sufficiently rigid so as not to reproduce the curvature of said patient implanted spinal correction rod implant, via said spacers, when said end contact parts are contacting said patient implanted spinal correction rod implant. This way, all differences between on the one side the surgery control tool curvature and on the other side the patient implanted spinal correction rod implant curvature will be seen at first glance by the surgeon because the surgeon will see that part of the surgery control tool end parts do not contact anymore the patient implanted spinal correction rod implant.

Preferably, most of, preferably all of, said spacers extending from said elongated body, are disposed along said elongated body, preferably regularly disposed along said elongated body. This way, all parts of patient implanted spinal correction rod implant are treated similarly and no part of said elongated body will be neglected.

Preferably, at least one of said spacers disposed along said elongated body is a reference spacer adapted to be located at a specific spot relative to a predetermined vertebra along patient spine. This way, the reference spacer allows for the surgeon to wedge very precisely the surgery control tool relative to the patient implanted spinal correction rod implant.

Preferably, it comprises at least 3 spacers per region of said elongated body presenting a curvature of same convexity. This way, each curvature of same convexity is precisely taken into account by the surgery control tool, none of them being neglected.

Preferably, only part of said contact end parts include each a fastening part so as to be able to be removably fastened to said patient implanted spinal correction rod implant. This way, the surgery control tool is more flexible and can adapt to more defects of the patient implanted spinal correction rod implant, for example adapt to residual Cobb angle error, while the surgery control tool remains firmly held in place relative to the patient implanted spinal correction rod implant.

Preferably, only two of said contact end parts, respectively located at opposite extremities of said elongated body, include each a fastening part so as to be able to be removably fastened to said patient implanted spinal correction rod implant. This way, the surgery control tool is all the more flexible and can all the more adapt to most of or event to all of defects of the patient implanted spinal correction rod implant, for example adapt to residual Cobb angle error, while the surgery control tool remains still rather firmly held in place relative to the patient implanted spinal correction rod implant.

Preferably, most of, preferably all of, said end contact parts are able to slide laterally relative to said elongated body longitudinal direction, when being in contact with said patient implanted spinal correction rod implant. This way, the surgery control tool is all the more flexible and can all the more adapt to most of or event to all of defects of the patient implanted spinal correction rod implant, for example adapt to residual Cobb angle error.

Preferably, most of, preferably all of, said end contact parts are able to slide laterally relative to said elongated body longitudinal direction, when having only a contact point with said patient implanted spinal correction rod implant. This way, the surgery control tool is made more precise and more stable than it would be if the contact surface was greater.

Preferably, either said elongated body is two dimensional and sliding range is less than 5 cm, or said elongated body is three dimensional and sliding range is less than 3 cm. This way, sliding range is adapted to the global shape of elongated body, so as to be simultaneously sufficiently small for being able to contact a patient implanted spinal correction rod implant not easily reachable and sufficiently big for being able to adapt to most of or event to all of defects of the patient implanted spinal correction rod implant, for example adapt to residual Cobb angle error.

Preferably, it has the shape and the size of a patient specific spinal correction rod. This way, being fully patient specific, the surgery control tool will be more precise and more useful to the surgeon.

Preferably, it has the length and the curvature of a patient specific spinal correction rod. This way, being closer to patient spinal correction rod implant shape and size, as far as the more interesting parameters are concerned, length and curvature, the surgery control tool will be more precise and more useful to the surgeon.

Preferably, said patient specific spinal correction rod includes one or more among following patient specific spinal corrections or modifications: Cobb angle correction, Kyphosis angle modification, Lordosis angle modification, Vertebral rotation correction. This way, the most important parameters related to patient spine scoliosis correction are taken into account by the surgery control tool.

Preferably, it is made of plastic. This is a cheap, light and sufficiently rigid material to get at an effective surgery control tool.

Preferably, it is a 3D printed plastic rod. This is a simple and cost effective way to manufacture the corresponding surgery control tool.

Preferably, said 3D printed plastic rod is in 2 or 3 portions which can be fastened together, preferably via a quick quarter turn fastener. This way, even quite long surgery control tools can be made, while being able to be stored and to be transported quite easily.

Preferably, it is made of resin, preferably of epoxy resin. This is a cheap, light and sufficiently rigid material to get at an effective surgery control tool.

Preferably, it is a resin rod manufactured by 3D photolithography. This is a simple and cost effective way to manufacture the corresponding surgery control tool.

Preferably, it is made of polyamide, preferably of PA2200. This is a cheap, light and sufficiently rigid material to get at an effective surgery control tool.

Preferably, it is a polyamide rod manufactured by selective laser sintering. This is a simple and cost effective way to manufacture the corresponding surgery control tool.

Preferably, it is a single use tool. This way, the surgery control tool can be made as patient specific as desired and as possible, to be as precise as desired or as possible, since it will be used only once for a single patient. So, it can be fully adapted to this single patient.

Preferably, on it are printed one or more among following information: a patient specific identification, a patient specific clinical parameter, a 3D orientation of said tool, a rod identification. This way, the most important pieces of information related to the patient and/or to the spinal correction rod implant to be implemented in this patient body, are printed on the surgery control tool itself so as to be directly and immediately available for the surgeon at all time.

Preferably, said spinal correction rod has the precise shape and the precise size of a spinal correction rod implant obtained from 3D spinal reconstruction got from two 2D X-ray patient images. This way, the surgery control tool will be made even more precise because even more patient specific, and this will be obtained at reasonable costs, needing no very expensive patient specific step therefore.

Preferably, said tool is sterilized. This way, the surgery control tool can be used directly and without any problem in the operative room by the surgeon while performing operation on the patient. The surgery control tool may be sterilized by gamma sterilization.

Preferably, said tool length ranges from 10 cm to 70 cm, preferably ranges from 20 cm to 50 cm. This way, the surgery control tool can account either for a full length spinal correction rod implant going from top thoracic vertebra T1 to bottom lumbar vertebra L5 or even to sacral plate S1, or at least for most of such length.

Preferably, number of said spacers ranges from 4 to 12, preferably from 5 to 10. This way, a good compromise between stability for the surgery control tool and visibility for the surgeon is met.

Further features and advantages of the invention will appear from the following description of embodiments of the invention, given as non-limiting examples, with reference to the accompanying drawings listed hereunder.

DETAILED DESCRIPTION OF THE INVENTION

Figure 1:
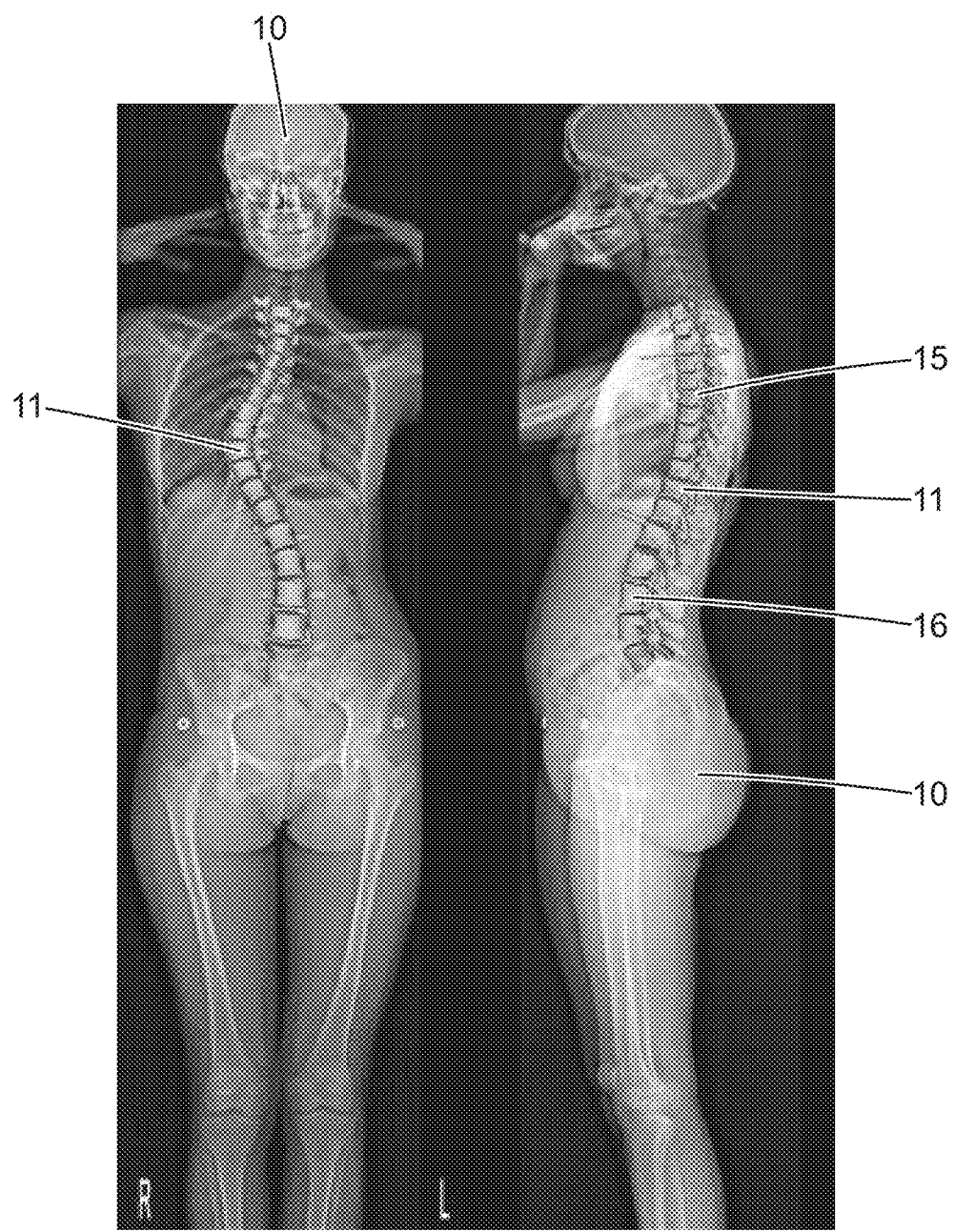
FIG. 1 shows an example of a patient radiography and 3D modeling, both frontal view on the left side and sagittal view on the right side, showing patient spine suffering from a scoliosis.

FIG. 1 shows an example of a patient radiography and 3D modeling, both frontal view on the left side and sagittal view on the right side, showing patient spine suffering from a scoliosis. The patient 10 can be seen as well as her or his patient vertebral spine 11.

On the left side of FIG. 1, when looking at the frontal view of the patient spine, if the patient was in good health, one should see a straight patient vertebral spine, which is not at all the case. On the contrary, patient vertebral spine 11 shows, in the frontal plane, a big curvature corresponding to an important scoliosis. This important scoliosis is to be corrected by implementing, respectively on both sides of this patient spine 11, two spinal correction rod implants which will straighten this curved patient spine 11.

On the right side of FIG. 1, when looking at the sagittal view of the patient spine, if the patient was in good health, one should see a patient vertebral spine corresponding to a typical kyphosis for upper part 15 of patient spine 11 and to a typical lordosis for lower part 16 of patient spine 11, what is not exactly the case. These incorrect kyphosis and lordosis are to be corrected by implementing, respectively on both sides of this patient spine 11, two spinal correction rod implants which will change the respective curvatures of kyphosis and lordosis of this patient spine 11.

Figure 2:
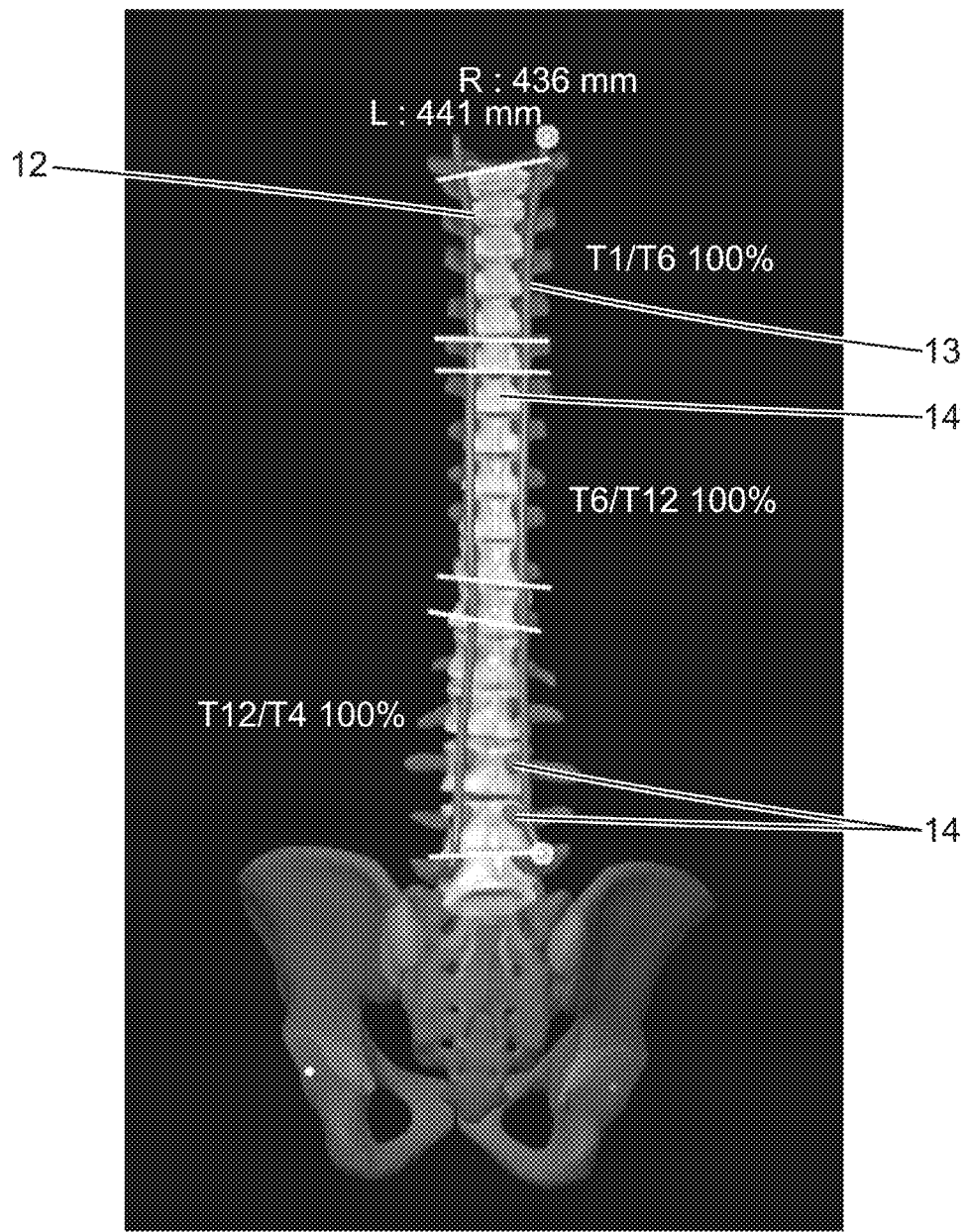
FIG. 2 shows an example of a 3D modeling, posterior view, showing patient spine previously suffering from a scoliosis but now straightened by two spinal correction rod implants.

FIG. 2 shows an example of a 3D modeling, posterior view, showing patient spine previously suffering from a scoliosis but now straightened by two spinal correction rod implants.

The important scoliosis, which could be seen on FIG. 1, was corrected by implementing, respectively on both sides of this patient spine 11, two spinal correction rod implants 12 and 13 which have straightened this curved patient spine 11. Both spinal correction rod implants 12 and 13 are fixed on patient spine 11 by screws 14. The screws 14 have been screwed in the vertebra of patient spine 11. The head of each screw 14 includes a slit in which the spinal correction rod implant 12 or 13 is held in place. Both spinal correction rod implants 12 and 13, being fixed on patient spine 11 by screws 14, and being straight and rigid because being made of metal, exert a constraint on patient spine 11, thereby straightening patient spine 11.

Figure 3:
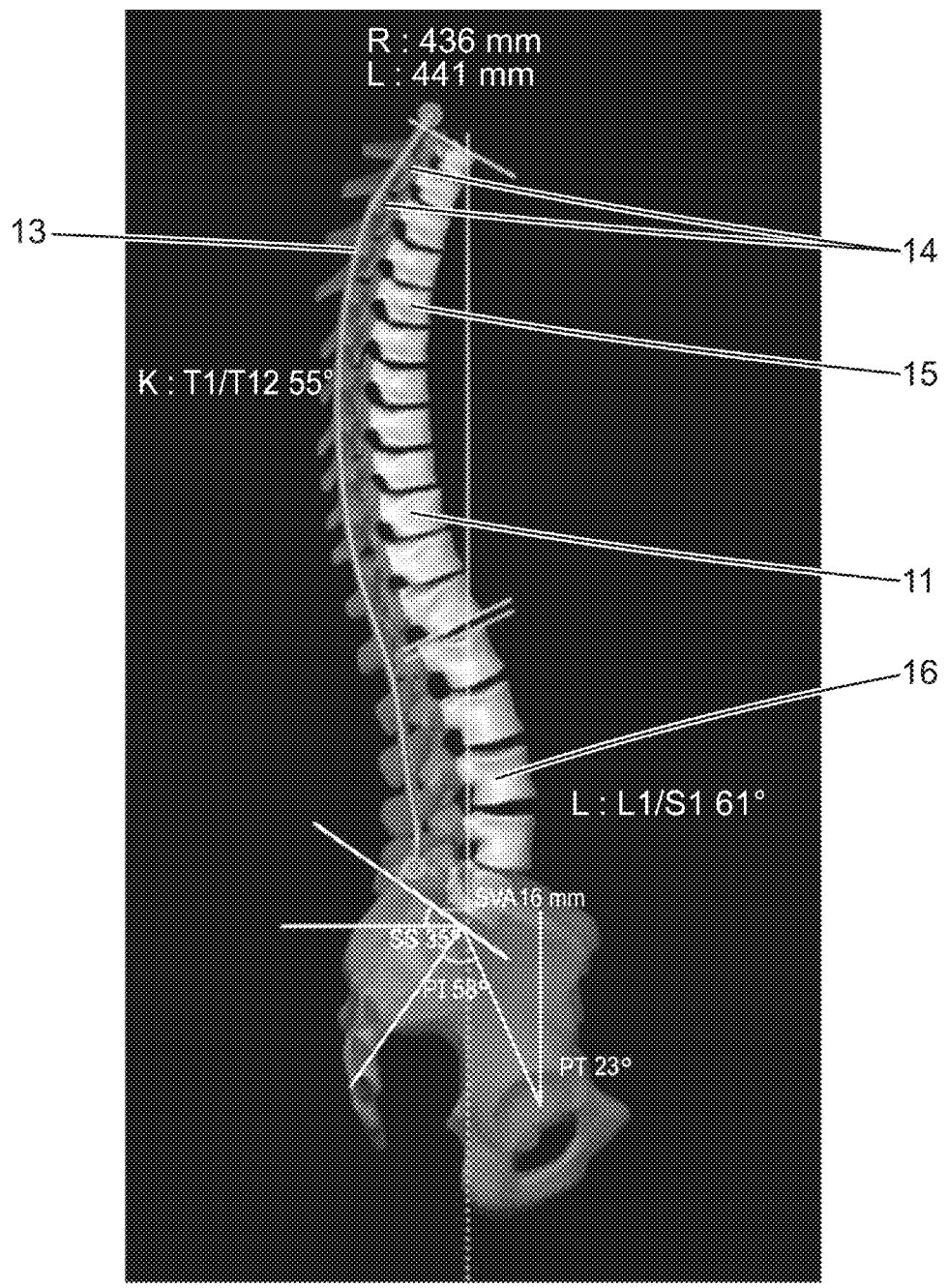
FIG. 3 shows an example of a 3D modeling, sagittal view, showing patient spine previously suffering from a scoliosis but now straightened by two spinal correction rod implants.

FIG. 3 shows an example of a 3D modeling, sagittal view, showing patient spine previously suffering from a scoliosis but now straightened by two spinal correction rod implants.

The incorrect kyphosis and lordosis, which could be seen on FIG. 1, were corrected by implementing, respectively on both sides of this patient spine 11, two spinal correction rod implants 12 and 13 (only spinal correction rod implant 13 can be seen on FIG. 3) which have changed the respective kyphosis and lordosis curvatures of this curved patient spine 11. Both spinal correction rod implants 12 and 13 are fixed on patient spine 11 by screws 14. The screws 14 have been screwed in the vertebra of patient spine 11. The head of each screw 14 includes a slit in which the spinal correction rod implant 12 or 13 is held in place. Both spinal correction rod implants 12 and 13, being fixed on patient spine 11 by screws 14, and being correctly curved and rigid because being made of metal, exert a constraint on patient spine 11, thereby changing and making correct the respective kyphosis and lordosis curvatures of respectively the upper part 15 and lower part 16 of this curved patient spine 11.

Figure 4:
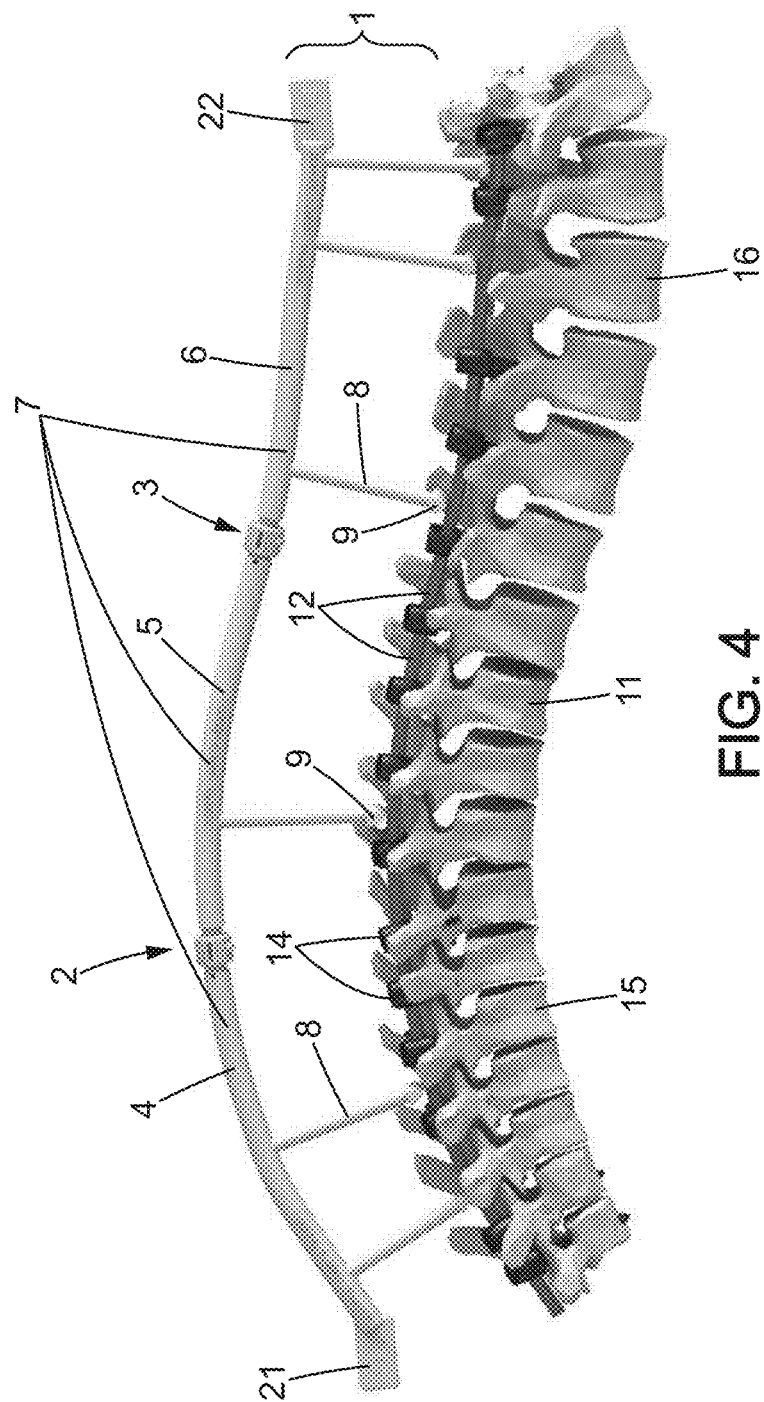
FIG. 4 shows an example of a side prone view of a surgery control tool used together with a patient implanted spinal correction rod implant according to a first embodiment of the invention.

FIG. 4 shows an example of a side prone view of a surgery control tool used together with a patient implanted spinal correction rod implant according to a first embodiment of the invention.

The spinal correction rod implant 12 is fixed within the slits of the screws 14 which are screwed into the patient spine 11. The surgery control tool 1 is put on this patient implemented spinal correction rod implant 12, for the surgeon to see whether all end contact parts 9 do contact or not the spinal correction rod implant 12. If they do, spinal correction rod implant 12 presents the right curvature, and the right length too. If they don't, spinal correction rod implant 12 doesn't present the right curvature, and maybe neither the right length.

Once the surgery control is made with control software, the lengths and shapes of the rods as implemented in patient body are used to produce the control templates which are the surgery control tools 1. These control templates are 3D printed and then sterilized, for instance with gamma ray sterilization, and sent to the hospital for the surgery control phase.

The surgery control tool 1 is no patient implant. The surgery control tool 1 comprises an elongated body 7 which includes at least a portion having the shape and the size of a spinal correction rod 12. Here, this elongated body 7 as a whole has the shape and the size of the spinal correction rod implant 12 it represents. This elongated body 7 has the length and the curvature of the spinal correction rod implant 12 it represents.

The surgery control tool 1 includes several spacers 8 extending orthogonally from elongated body 7 and being terminated by end contact parts 9 disposed to contact the patient implemented spinal correction rod implant 12. Preferably spacers 8 extend also orthogonally from patient implemented spinal correction rod implant 12.

The surgery control tool 1 is a 3D (three dimensional) printed plastic rod which is in three parts, an upper part 4, a middle part 5 and a lower part 6. The upper part 4 and middle part 5 can be fastened together, via a quick quarter turn fastener 2. The middle part 5 and the lower part 6 can be fastened together, via a quick quarter turn fastener 3.

The surgery control tool 1, which is the control template, can have a length too long to be printed in one part, thus this template can be printed in three parts 4, 5 and 6, and the three parts 4 to 6 are assembled during the surgery preparation using printed fixation parts 2 and 3 such as a quick quarter turn fasteners.

On the end of upper part 4, there may be written a first piece of information about patient and/or patient spinal correction which has been etched in the plastic. On the end of lower part 6, there may be written a piece of information about patient and/or patient spinal correction which has been etched in the plastic. In the middle of middle part 5, there may be written a piece of information about patient and/or patient spinal correction which has been etched in the plastic.

At upper end of surgery tool 1, there is an upper plate 21 which first indicates it is the upper end and which second allows for the surgeon to more easily manipulate the surgery control tool 1, by holding this upper plate 21 firmly and precisely between her or his fingers, the plan of this upper plate 21 being in the sagittal plane of the surgery control tool 1. At lower end of surgery tool 1, there is a lower plate 22 which first indicates it is the lower end and which second allows for the surgeon to more easily manipulate the surgery control tool 1, by holding this lower plate 22 firmly and precisely between her or his fingers, the plan of this lower plate 22 being in the sagittal plane of the surgery control tool 1 and being in the same plan as the upper plate 21.

The spinal correction rod implant 12 is fixed within the slits of the screws 14 which are screwed into the patient spine 11. The surgery control tool 1 is put on this patient implemented spinal correction rod implant 12, for the surgeon to see whether all end contact parts 9 do contact or not the spinal correction rod implant 12. If they do, spinal correction rod implant 12 presents the right curvature, and the right length too. If they don't, spinal correction rod implant 12 doesn't present the right curvature, and maybe neither the right length.

By visually checking whether the end contact parts 9 are or are not in contact with the patient implemented spinal correction rod implant 12, the surgeon may see which part of the patient implemented spinal correction rod implant 12 still needs further over and/or under bending (and/or further cutting), for example over bending in a first plane and under bending in a second plane different from first plane, in order to perform such over and/or under bending either in situ, if bending range is limited, or outside patient by taking it out if bending range too important. Afterwards, by again visually checking if the end contact parts 9 are all or practically all in contact with the patient implemented spinal correction rod implant 12, the surgeon may decide that the patient implemented spinal correction rod implant 12 is satisfactory with respect to its curvature and to its length.

Figure 5:
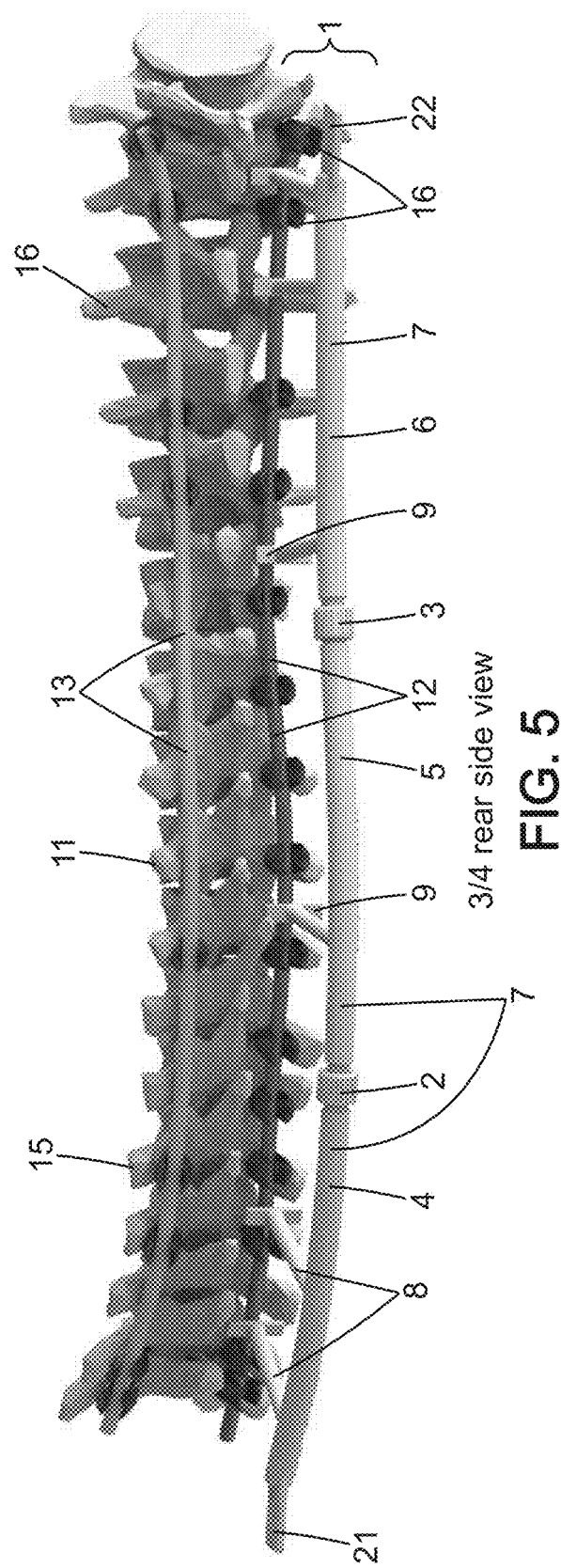
FIG. 5 shows an example of a ¾ rear side view of a surgery control tool used together with a patient implanted spinal correction rod implant according to a first embodiment of the invention.

FIG. 5 shows an example of a ¾ rear side view of a surgery control tool used together with a patient implanted spinal correction rod implant according to a first embodiment of the invention. All elements, having same references as on FIG. 4, are the same as on FIG. 4.

Figure 6:
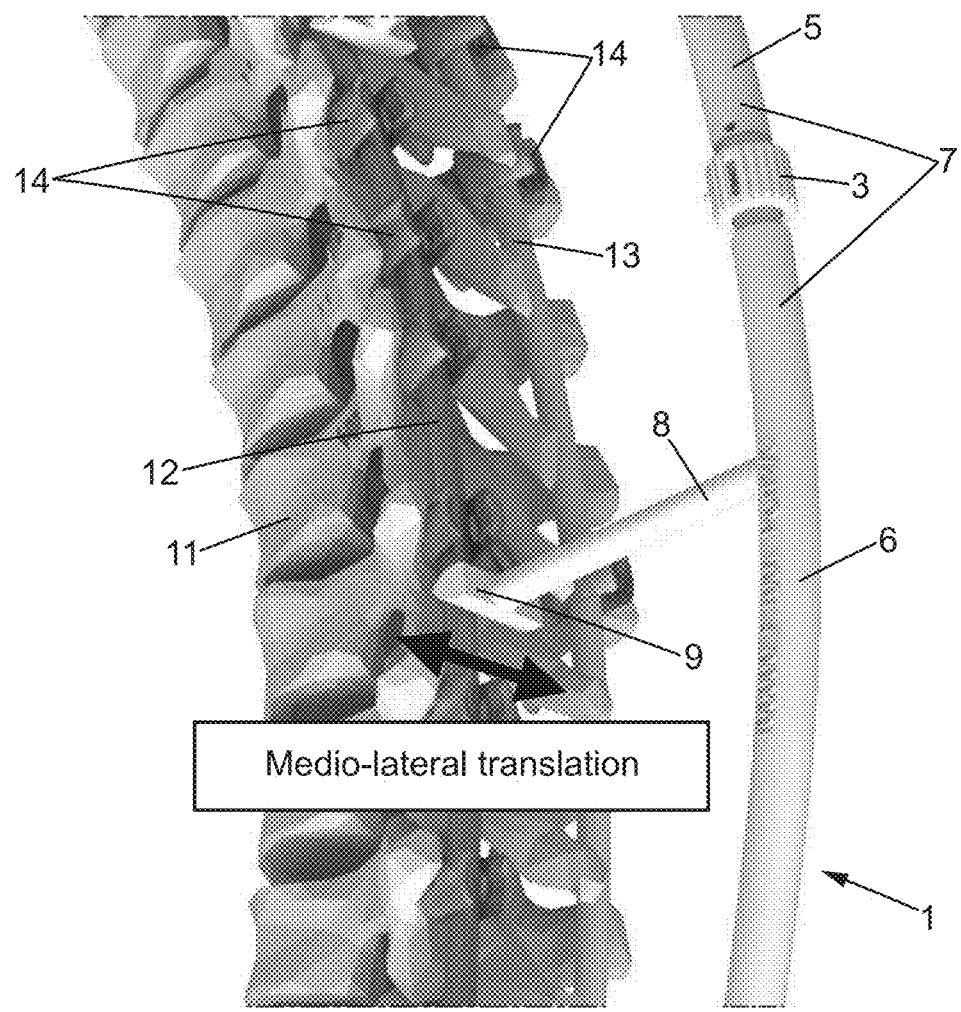
FIG. 6 shows a detail of an example of a perspective view of a surgery control tool used together with a patient implanted spinal correction rod implant according to a first embodiment of the invention.

FIG. 6 shows a detail of an example of a perspective view of a surgery control tool used together with a patient implanted spinal correction rod implant according to a first embodiment of the invention.

When the surgery control tool 1 is set on the patient implemented spinal correction rod implant 12, first the longitudinal mobility of the spacers 8 relative to the elongated body 7 (not represented on FIG. 6 for clarity reasons) allow for them to avoid bumping into the heads of the screws 14, and second the lateral mobility (represented on FIG. 6) of end contact parts 9 terminating spacers 8 relative to the elongated body 7 as well as relative to the patient implemented spinal correction rod implant 12, allow for them to adapt to slight lateral mismatch between surgery control tool 1 and patient implemented spinal correction rod implant 12. This lateral mobility of end contact parts 9 is represented on FIG. 6 by a double arrow, since this lateral mobility is in both opposite directions, and is noted "medio-lateral translation". End contact parts 9 preferably are end contact pines 9. The extremity of the end contact pin 9 is a kind of conic cylinder able to provide a medio-lateral degree of freedom to manage the residual Cobb's angle.

Figure 7:
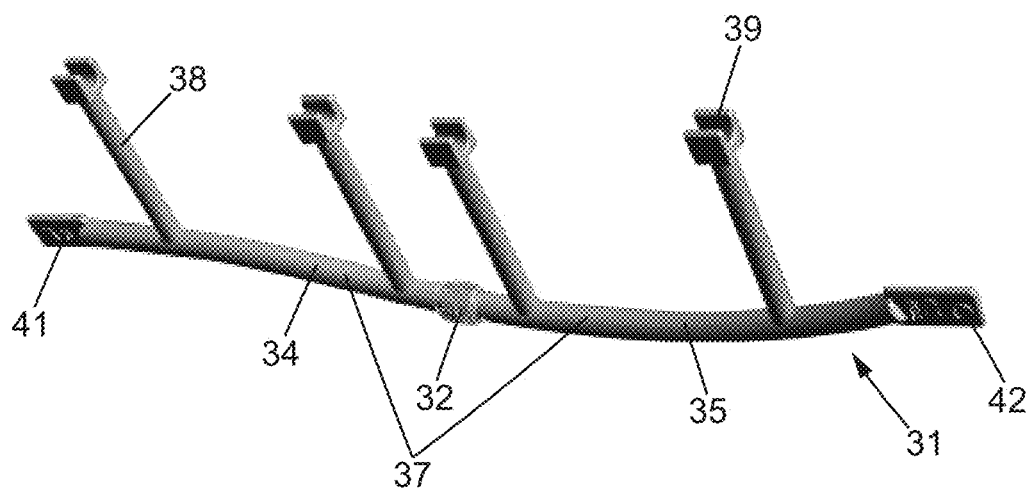
FIG. 7 shows an example of a perspective view of a surgery control tool used together with a patient implanted spinal correction rod implant according to a second embodiment of the invention.

FIG. 7 shows an example of a perspective view of a surgery control tool used together with a patient implanted spinal correction rod implant according to a second embodiment of the invention.

The surgery control tool includes several spacers 38 extending orthogonally from elongated body 37 and being terminated by end contact parts 39 disposed to contact the patient implemented spinal correction rod implant. Spacers 38 do not extend orthogonally from patient implemented spinal correction rod implant. End contact parts 39 are U shaped so as to be able to be fastened on patient implemented spinal correction rod implant, the U shape of each end contact part 39 coming around the patient implemented spinal correction rod implant.

The surgery control tool is a 3D (three dimensional) printed plastic rod which is in two parts, an upper part 34 and a lower part 35. The upper part 34 and the lower part 35 can be fastened together, via a quick quarter turn fastener 32.

The surgery control tool, which is the control template, can have a length too long to be printed in one part, thus this template can be printed in two parts 34 and 35, and the two parts 34 and 35 are assembled during the surgery preparation using printed fixation part 32 such as a quick quarter turn fastener.

On the end of upper part 34, there may be written a first piece of information about patient and/or patient spinal correction which has been etched in the plastic. On the end of lower part 35, there may be written a piece of information about patient and/or patient spinal correction which has been etched in the plastic.

At upper end of surgery tool, there is an upper plate 41 which first indicates it is the upper end and which second allows for the surgeon to more easily manipulate the surgery control tool 1, by holding this upper plate 41 firmly and precisely between her or his fingers, the plan of this upper plate 41 being in the sagittal plane of the surgery control tool. At lower end of surgery tool, there is a lower plate 42 which first indicates it is the lower end and which second allows for the surgeon to more easily manipulate the surgery control tool, by holding this lower plate 42 firmly and precisely between her or his fingers, the plan of this lower plate 42 being in the sagittal plane of the surgery control tool and being in the same plan as the upper plate 41.

This second embodiment is not preferred, since in case of slight lateral shift between surgery control tool and patient implemented spinal correction rod implant, it becomes more difficult to fasten all end contact parts 39 around this patient implemented spinal correction rod implant. This second embodiment does not present any medio-lateral translation degree of freedom, and will be therefore less precise in presence of a residual Cobb angle, which residual Cobb angle is rather common.

Figure 8:
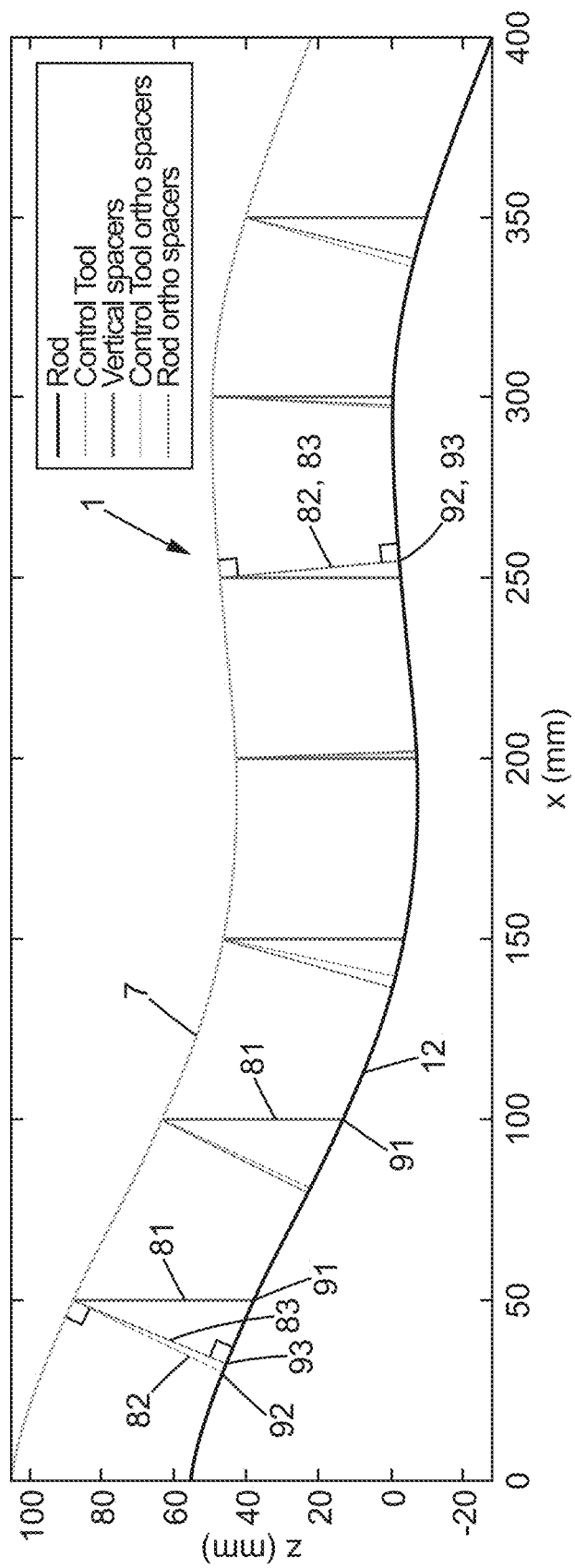
FIG. 8 shows examples of a schematic representation of surgery control tool spacers' dispositions according to three possible spacers' embodiments of the invention.

FIG. 8 shows examples of a schematic representation of surgery control tool spacers' dispositions according to three possible spacers' embodiments of the invention.

The elongated body 7 of the surgery control tool 1 is represented put on the patient implemented spinal correction rod implant 12. A parameter z is represented as a function of another parameter x, both being expressed in mm. Parameter x corresponds indeed to the height of the patient spine, whereas parameter z corresponds to horizontal shift in a sagittal plane of the patient spine. Here, three different possible configurations of spacers with their end contact parts are represented.

In a first embodiment, spacers 81 extend vertically from surgery control tool 1 to patient implemented spinal correction rod implant 12, since patient is laid down horizontally on front part of body when being operated by surgeon. Spacers 81 are terminated by end contact 91 contacting or supposed to contact patient implemented spinal correction rod implant 12.

In a second embodiment, spacers 82 extend orthogonally from surgery control tool 1 to patient implemented spinal correction rod implant 12. Patient is laid down horizontally on front part of body when being operated by surgeon. Spacers 82 are terminated by end contact 92 contacting or supposed to contact patient implemented spinal correction rod implant 12.

In a third embodiment, spacers 83 extend from surgery control tool 1 to arrive orthogonally on patient implemented spinal correction rod implant 12. Patient is laid down horizontally on front part of body when being operated by surgeon. Spacers 83 are terminated by end contact 93 contacting or supposed to contact orthogonally patient implemented spinal correction rod implant 12.

Figure 9:
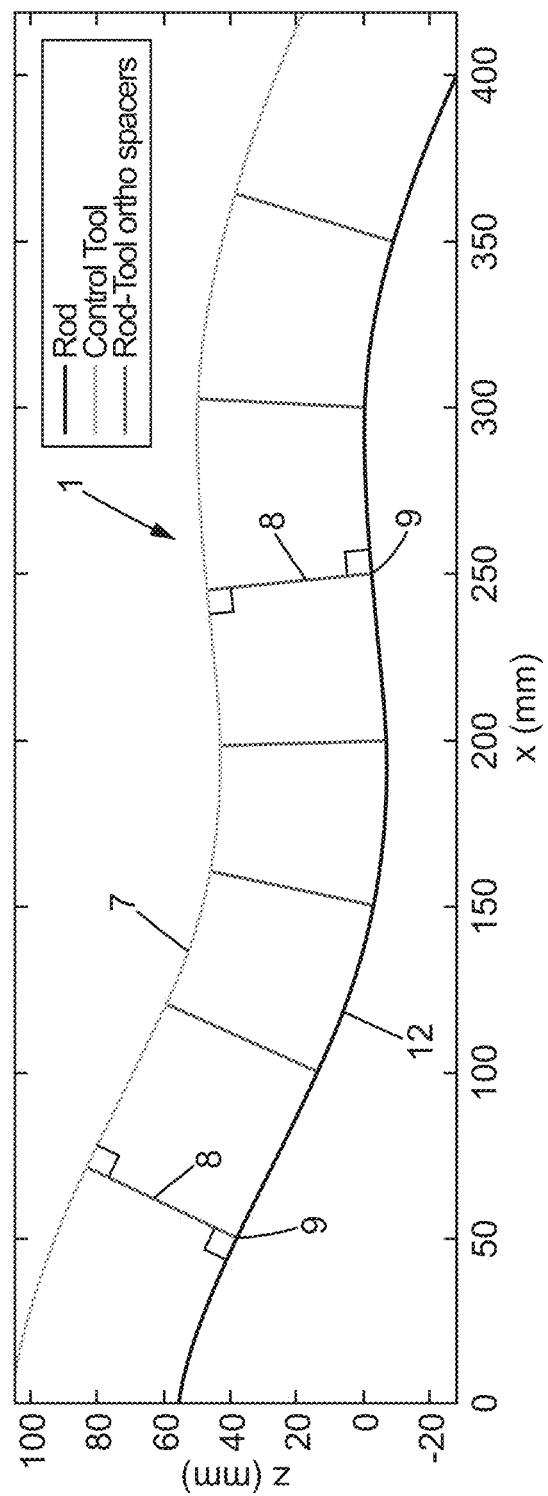
FIG. 9 shows an example of a schematic representation of another surgery control tool spacers' disposition according to a fourth possible spacer embodiment of the invention.

FIG. 9 shows an example of a schematic representation of another surgery control tool spacers' disposition according to a fourth possible spacer embodiment of the invention.

The elongated body 7 of the surgery control tool 1 is represented put on the patient implemented spinal correction rod implant 12. A parameter z is represented as a function of another parameter x, both being expressed in mm. Parameter x corresponds indeed to the height of the patient spine, whereas parameter z corresponds to horizontal shift in a sagittal plane of the patient spine. Here, a fourth preferred embodiment of spacers with their end contact parts is represented.

In this fourth embodiment, spacers 8 extend orthogonally from surgery control tool 1 to also arrive orthogonally on patient implemented spinal correction rod implant 12. Patient is laid down horizontally on front part of body when being operated by surgeon. Spacers 83 are terminated by end contact 93 contacting or supposed to contact orthogonally patient implemented spinal correction rod implant 12. This fourth embodiment of spacers 8 gives the best precision for the surgery control tool 1, as well as, if applicable, the best range of mobility without additional error, and is therefore preferred.

The invention has been described with reference to preferred embodiments. However, many variations are possible within the scope of the invention.

The invention claimed is:

1. Surgery control tool:
   being no patient implant,
   comprising:
   an elongated body (7, 37) having the shape and the size of a spinal correction rod,
   end contact parts (9, 39) being able to contact a patient implanted spinal correction rod implant (12, 13),
   spacers (8, 38) extending from said elongated body (7, 37) towards said end contact parts (9, 39), wherein said elongated body (7, 37) is sufficiently rigid so as not to reproduce the curvature of said patient implanted spinal correction rod implant (12, 13), via said spacers (8, 38), when
   said end contact parts (9, 39) are contacting said patient implanted spinal correction rod implant (12, 13).

2. Surgery control tool, according to claim 1, wherein most of said spacers (8, 38) extending from said elongated body (7, 37), extend orthogonally from said elongated body (7, 37), and wherein most of said spacers (8, 38) extending from said elongated body (7, 37), have different lengths depending on the curvature radius respectively at their junction points with said elongated body (7, 37).

3. Surgery control tool, according to claim 1, wherein most of said spacers (8, 38) extending from said elongated body (7, 37), extend both orthogonally from said elongated body (7, 37) and orthogonally from said patient implanted spinal correction rod implant (12, 13), and wherein most of said spacers (8, 38) extending orthogonally from said elongated body (7, 37) and orthogonally from said patient implanted spinal correction rod implant (12, 13), have the same length.

4. Surgery control tool, according to claim 1, wherein most of said spacers (8, 38) disposed along said elongated body (7, 37), are longitudinally mobile relative to said elongated body (7, 37), and wherein said longitudinal mobility range is less than 8 mm, and/or wherein said longitudinal mobility range is more than 2 mm.

5. Surgery control tool, according to claim 1, wherein most of said spacers (8, 38) extending from said elongated body (7, 37), are disposed along said elongated body (7, 37).

6. Surgery control tool, according to claim 1, wherein at least one of said spacers (8, 38) disposed along said elongated body (7, 37) is a reference spacer adapted to be located at a specific spot relative to a predetermined vertebra along patient spine (11).

7. Surgery control tool, according to claim 1, further comprising at least 3 spacers (8, 38) per region of said elongated body (7, 37) presenting a curvature of same convexity.

8. Surgery control tool, according to claim 1, wherein most of said end contact parts (9, 39) are able to slide laterally relative to said elongated body (7, 37) longitudinal direction, when being in contact with said patient implanted spinal correction rod implant (12, 13), or wherein most of said end contact parts (9, 39) are able to slide laterally relative to said elongated body (7, 37) longitudinal direction, when having only a contact point with said patient implanted spinal correction rod implant (12, 13).

9. Surgery control tool, according to claim 8, wherein:
either said elongated body (7, 37) is two dimensional and sliding range is less than 5 cm,
or said elongated body (7, 37) is three dimensional and sliding range is less than 3 cm.

10. Surgery control tool according to claim 1, having the shape and the size and the length and the curvature of a patient specific spinal correction rod.

11. Surgery control tool according to claim 10, wherein said patient specific spinal correction rod includes one or more among following patient specific spinal corrections or modifications:
Cobb angle correction,
Kyphosis angle modification,
Lordosis angle modification,
Vertebral rotation correction.

12. Surgery control tool according to claim 1, comprising plastic, or wherein the surgery control tool is a 3D printed plastic rod.

13. Surgery control tool according to claim 1, comprising resin.

14. Surgery control tool according to claim 1, comprising polyamide.

15. Surgery control tool according to claim 1, wherein the surgery control tool is a single use tool and/or wherein said tool (1) is sterilized.

16. Surgery control tool according to claim 1, wherein on the surgery control tool are printed one or more among following information:
a patient specific identification,
a patient specific clinical parameter,
a 3D orientation of said tool,
a rod identification.

17. Surgery control tool according to claim 1, wherein said spinal correction rod has the precise shape and the precise size of a spinal correction rod implant (12, 13) obtained from 3D spinal reconstruction got from two 2D X-ray patient images.

18. Surgery control tool according to claim 1, wherein said tool (1) length ranges from 10 cm to 70 cm.

19. Surgery control tool according to claim 1, wherein number of said spacers (8, 38) ranges from 4 to 12.

20. Surgery control tool:
being no patient implant,
comprising:
an elongated body (7, 37) having the shape and the size of a spinal correction rod,
end contact parts (9, 39) being able to contact a patient implanted spinal correction rod implant (12, 13),
spacers (8, 38) extending from said elongated body (7, 37) towards said end contact parts (9, 39);
wherein most of said spacers (8, 38) extending from said elongated body (7, 37), extend parallel to one another; and
wherein most of said spacers (8, 38) extending from said elongated body (7, 37), extend vertically when said surgery control tool end contact parts (9, 39) contact said patient implanted spinal correction rod implant (12, 13).

21. Surgery control tool, according to claim 20, wherein most of said spacers (8, 38) extending from said elongated body (7, 37), have the same length.

22. Surgery control tool, according to claim 20, wherein most of said spacers (8, 38) disposed along said elongated body (7, 37), are longitudinally immobile relative to said elongated body (7, 37).

23. Surgery control tool:
being no patient implant,
comprising:
an elongated body (7, 37) having the shape and the size of a spinal correction rod,
end contact parts (9, 39) being able to contact a patient implanted spinal correction rod implant (12, 13),
spacers (8, 38) extending from said elongated body (7, 37) towards said end contact parts (9, 39);
wherein only part of said end contact parts (9, 39) include each a fastening part so as to be able to be removably fastened to said patient implanted spinal correction rod implant (12, 13), and
wherein only two of said end contact parts (9, 39), respectively located at opposite extremities of said elongated body (7, 37), include each a fastening part so as to be able to be removably fastened to said patient implanted spinal correction rod implant (12, 13).

* * * * *